(12) United States Patent
Koltermann et al.

(10) Patent No.: US 8,817,091 B2
(45) Date of Patent: Aug. 26, 2014

(54) APPARATUS FOR MONITORING A PRINT RESULT IN A ROTARY PRINTING PRESS

(75) Inventors: Oliver Koltermann, Enger (DE); Dirk Volkening, Petershagen (DE)

(73) Assignee: eltromat GmbH, Leopoldshöhe (DE)

( * ) Notice: Subject to any disclaimer, the term of this patent is extended or adjusted under 35 U.S.C. 154(b) by 392 days.

(21) Appl. No.: 13/180,091

(22) Filed: Jul. 11, 2011

(65) Prior Publication Data

US 2012/0013733 A1 Jan. 19, 2012

(30) Foreign Application Priority Data

Jul. 15, 2010 (DE) .................... 20 2010 008 084 U

(51) Int. Cl.
*G01N 19/08* (2006.01)
*B41F 33/00* (2006.01)

(52) U.S. Cl.
CPC ......... *B41F 33/0036* (2013.01); *B41F 33/0009* (2013.01)
USPC ............... 348/125; 348/88; 348/92; 382/141; 382/149

(58) Field of Classification Search
CPC . G01N 21/89; G01N 21/8901; G01N 21/896; G01N 21/88; G01N 21/956; G01N 21/86; G01N 21/8903; G06T 2207/30124; G06T 2207/30144; G06T 2207/30168; G06T 7/0004; B65H 2515/84; B65H 2553/42; B65H 26/02; B65H 2511/512; B41F 33/0081; B41F 33/00
USPC .......... 250/559.44; 702/82; 101/485; 348/88, 348/92, 125; 382/141, 149
See application file for complete search history.

(56) References Cited

U.S. PATENT DOCUMENTS

| | | | | |
|---|---|---|---|---|
| 5,256,883 A * | 10/1993 | Weichmann et al. | ..... | 250/559.39 |
| 5,696,591 A * | 12/1997 | Bilhorn et al. | ................ | 356/429 |
| 5,774,225 A | 6/1998 | Goldstein et al. | | |
| 6,535,621 B1 * | 3/2003 | Fujita | ............................ | 382/112 |
| 6,621,585 B1 * | 9/2003 | Patel et al. | .................... | 358/1.12 |
| 6,765,224 B1 * | 7/2004 | Favreau et al. | ............ | 250/559.4 |
| 6,874,420 B2 * | 4/2005 | Lewis et al. | .................... | 101/485 |
| 7,040,232 B2 * | 5/2006 | Van Holten et al. | .......... | 101/484 |
| 8,000,501 B2 * | 8/2011 | Huotilainen | .................. | 382/108 |
| 2003/0117492 A1 * | 6/2003 | Jokela | ............................ | 348/88 |
| 2004/0107061 A1 * | 6/2004 | Ruuska | .......................... | 702/82 |
| 2004/0188644 A1 * | 9/2004 | Rappette et al. | ......... | 250/559.44 |
| 2009/0060316 A1 * | 3/2009 | Ruuska | ........................ | 382/141 |

FOREIGN PATENT DOCUMENTS

| | | |
|---|---|---|
| DE | 4321177 A1 | 1/1995 |
| DE | 102004044215 A1 | 12/2005 |
| DE | 102006022530 A1 | 11/2007 |

* cited by examiner

*Primary Examiner* — Sath V Perungavoor
*Assistant Examiner* — Nathnael Aynalem
(74) *Attorney, Agent, or Firm* — Richard M. Goldberg

(57) ABSTRACT

Apparatus for monitoring a print result in a rotary printing press, includes a web monitoring system including a matrix camera (20) that is movable in transverse direction over a web printed in the printing press, the matrix camera being adapted to capture an excerpt of the printed image in synchronism with a repeat of the printed image during a print run, an inspection system for a complete inspection of the printed image, the inspection system including a line camera that extends over the entire widths of the web, and an integrated control desk for the web monitoring system and the inspection system.

6 Claims, 2 Drawing Sheets

APPARATUS FOR MONITORING A PRINT RESULT IN A ROTARY PRINTING PRESS

BACKGROUND OF THE INVENTION

The invention relates to an apparatus for monitoring a print result in a rotary printing press, comprising:
- a web monitoring system including a matrix camera that is movable in transverse direction across a web being printed in the printing press, the matrix camera being adapted to capture an excerpt of a printed image in synchronism with a repeat of the printed image during a production run of the printing press; and
- an inspection system for a complete inspection of the printed image, said inspection system including a line camera that extends over the entire width of the web.

For the printing industry, web monitoring systems have been known which permit to monitor a selected excerpt from the image printed onto the web during a production run. By synchronising the matrix camera with the repeat of the printed image it can be achieved that a stationary image which represents the selected excerpt of the printed image can be presented to the operator on a monitor. When the monitoring of this excerpt reveals that the printed image suffers from certain errors, e.g. register errors, the operator can re-adjust the pertinent settings of the printing press, such as the side register or the longitudinal register of individual colour decks, in order to correct these errors. Similarly, other setting parameters of the printing press may be re-adjusted in order to remedy other types of error, e.g. as the impression setting (the force with which the form cylinder is pressed against the web).

A control desk including at least one monitor and operating elements for controlling the matrix camera and for inputting the set operations that may be necessary for the printing press forms part of the web monitoring system.

Typically, the matrix camera has a zoom function, so that defective or problematic areas of the printed image can be assessed with high resolution.

However, the matrix camera permits only to monitor a relatively small fraction of the entire surface of the printed web, typically a fraction in the order of magnitude of about 1%. With a conventional web monitoring system, it is therefore not possible to reliably detect every error that occurs in the printed product.

Special inspection systems have been developed for a complete inspection of the printed product, these systems being capable of capturing a complete image of the printed web and storing the same in digital form. The image information is linked with positional information indicating the location of the respective image area in longitudinal direction of the web. A control desk with a monitor permits to retrieve, for any desired point on the printed web, the corresponding image and to inspect the same for errors. When non-tolerable errors are found in the printed image, it is possible on the basis of the stored positional information to access the defective portion of the printed web by means of a winder and to excise this portion from the web after the print run has been terminated.

Error recognition algorithms for automatically recognizing errors have also been developed. To that end, the first approximately 50 repeating printing images (formats), for example, are digitally captured with a line camera, and the image information is integrated over the 50 images, so that one obtains a reference image, the so-called "golden image" with which the images that are captured later during the print run are to be compared. In the integration phase, the range of variance of the image information may be determined for each pixel, so that tolerance limits for error recognition can be set. During the print run, the image that is currently being captured is subtracted from the reference image, and when the difference obtained is outside of the error tolerances, an error signal is generated and the defective image area is shown on the monitor of the control desk. This enables the operator to intervene already during the print run in order to remove the error or, when the error is not removable, to abort the print run. Moreover, the positions of the image errors that have been recognized may be stored, so that the defective places on the printed web may deliberately be inspected after termination of the print run and may be removed if necessary. The final decision whether a defective image area is to be removed or can still be tolerated is still taken by the operating personal.

Until now, even when web monitoring systems and inspection systems are employed simultaneously with the same printing press, these systems are generally configured as separated, independent systems.

On the other hand, inspection systems have become known which have a high-resolution digital line camera the image signal of which can also be used for web monitoring. However, this line camera does not have an optical zoom function, so that the resolution is limited and problematic image areas may often not be inspected with the desired accuracy.

For an inspection system with automatic error recognition, there has already been developed an interface to a web monitoring system, which interface permits to alert the operator at the control desk of the web monitoring system of errors that have been recognized by the inspection system.

SUMMARY OF THE INVENTION

It is an object of the invention to provide an apparatus for monitoring the print result, which apparatus has a simplified configuration and can be operated more conveniently.

According to the invention, this object is achieved by an integrated control desk for the web monitoring system and the inspection system.

Thus, according to the invention, the functions that have heretofore been fulfilled by two separate control desks, are fulfilled with a single integrated control desk, so that the space and installation requirements are reduced and synergies between the two systems can be utilized more efficiently. In particular, operating parameters that are relevant to both systems, such as the width of the web or the repeat for the current print run, need to be input only once.

In principle, a single large-format high-resolution monitor screen is sufficient for reproducing the image captured with the matrix camera of the web monitoring system and the image captured by the inspection system, wherein, if necessary, both images can be represented in split-screen technique or as "image-in-image". The operator may select whether he wants to carry out the web monitoring with the line camera or with the matrix camera. In particular, there is the advantageous possibility to position the matrix camera such that it captures a particularly problematic image area, e.g. a bar code when printing packaging material, whereas the area for the web monitoring may be selected flexibly with the line camera. This permits to switch between two image areas without time delay during the web monitoring, so as to improve the monitoring quality.

Useful embodiments of the invention are indicated in the dependent claims.

In a particularly advantageous embodiment, the control desk has a touch-sensitive monitor screen (touch screen). The operating elements for the web monitoring system and the inspection system are then formed by soft keys on the screen, and the selection and arrangement of these operating elements may flexibly be adapted to the respective function to be performed.

BRIEF DESCRIPTION OF THE DRAWINGS

An embodiment example will now be explained in detail in conjunction with the drawings, wherein.

DETAILED DESCRIPTION

Figure 1:
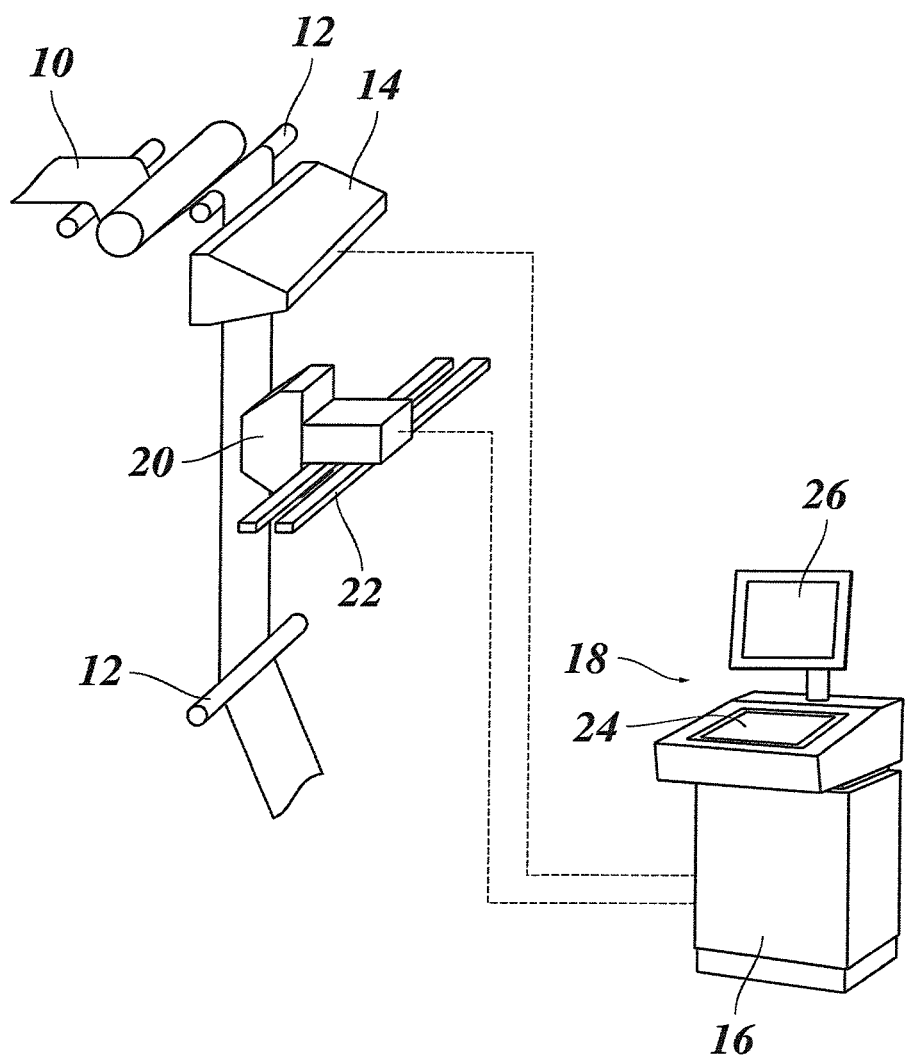
FIG. 1 is a schematic perspective view of an apparatus according to the invention.

In FIG. 1, there has been shown a portion of a web 10 that has been printed in a rotary printing press and is passed over several deflection and guide rollers 12 to a winder that has not been shown. On the printed side of the web, there is arranged a digital line camera 14 which extends transversely of the web 10 over the entire width thereof and is capable of sampling a complete colour image of a line of the image printed onto the web 10 at any point of time.

The line camera 14 is connected to a high performance electronic data processing system 16 in a control desk 18 of the apparatus. In the data processing system 16, the digital image data delivered by the line camera 14 are stored line by line, so that a complete image of the printed web 10 is captured in the course of the print run. In this process, the data processing system 16 receives also information from a control device of the printing machine, in particular information on the web transport, permitting to associate each area of the captured and stored image with a corresponding longitudinal position on the web 10. Moreover, the data processing system 16 includes a high performance image processing system and software for automatic error recognition.

Illumination systems (bright and dark field illumination) for illuminating, on the web 10, the image line captured by the line camera 14, are integrated in the line camera 14. Optionally, an illuminating device, e.g. a linear LED array, may also be disposed opposite to the line camera 14 on the back side of the web 10, so that it is possible to capture transparent webs also in a light transmission mode.

A matrix camera 20 adapted to take an image of a rectangular excerpt from the image printed onto the web 10 is also installed at the web 10. Again, corresponding illuminating devices are directly integrated in the camera.

In the rotary printing press, the web 10 is printed with an image that repeats itself in certain intervals (the repeat), i.e. at least after each complete revolution of the printing cylinders. In accordance with the principles of stroboscopy, the matrix camera 20 is synchronized with the repeat such that the same excerpt from the image is photographed digitally in each single shot of the matrix camera, so that a stationary image is obtained on a monitor screen on which the captured images are reproduced one after the other.

The matrix camera 20 may be displaced on rails 22 in transverse direction of the web 10, so that the lateral position of the image area to be photographed can be varied. By changing the phase of the image sequence relative to the repeat, the longitudinal position of the image area may also be varied. Moreover, the matrix camera 20 has an optical zoom which permits to zoom closer into the web 10 so that a smaller image area can be monitored with an increased resolution.

The matrix camera 20 is the core feature of a monitoring system which serves for randomly monitoring the result of the print process, so that the operator may intervene at any time in order to correct any possible errors such as register error, colour errors or the like.

In contrast, the line camera 14 is the core feature of an inspection system that serves for inspecting the entirety of the printed web 10 for possible errors in the printed image, so that defective areas may be excised from the web in a later step.

In the apparatus that has been shown here, the control desk 18 is an integrated control desk that is configured to control both the inspection system (line camera 14) and the web monitoring system (matrix camera 20) and to electronically process the data delivered by these systems and present them to the operating personal. To that end, the control desk 18 has a touch screen 24 which may selectively display an image generated by the line camera 14, an image generated by the matrix camera 20 or a combination of such images, along with image representations of keys for operating instructions. In the example shown, an additional monitor 26 is mounted on the control desk.

Figure 2:
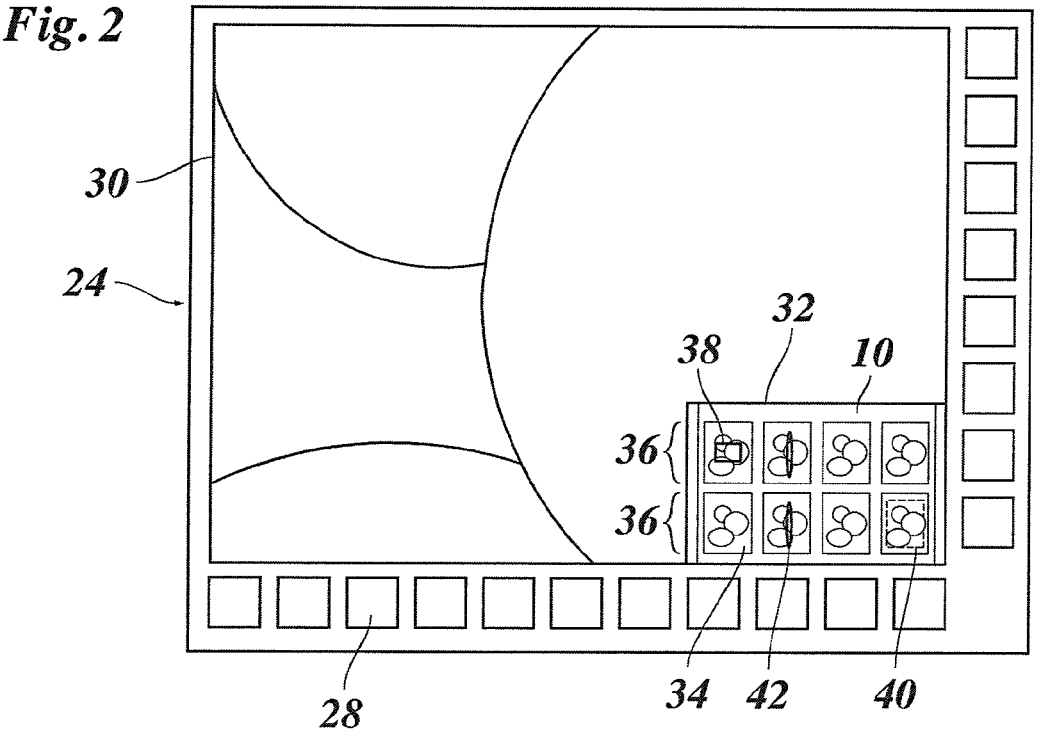
FIGS. 2 and 3 show examples for screen images on a monitor of a control desk of the apparatus according to FIG. 1.

FIG. 2 shows an example of a display image shown on the screen 24. Key areas 28 (soft keys) for the operating commands needed in the respective situation, e.g. for selecting the image reproduction mode, for positioning the matrix camera 20, and the like, are shown at the lower edge and at the right edge of the screen. The locations and contents of the key areas may be varied dynamically depending upon the functions to be performed and upon the operating condition. Optionally, there may also be provided keys for adjusting the longitudinal register and the side register, for the impression setting of the printing press, and the like.

In the example shown, an image window 30 shows an image area that has been selected for web monitoring. In the lower right corner of the image window 30 a smaller image 32 has been blended in which shows, in full width, a section of the web 10 as it is actually captured with the line camera 14. In the example shown, the image printed onto the web 10 is composed of four blanks 34 which have identical image contents and are distributed over the width of the web. In the example shown, the web section reproduced in the image 32 has a length of two formats 36 (a format is the repeating image that is printed in each revolution of the printing cylinders).

A frame 38 in the image 32 indicates the location and size of the image area that is being used for the web monitoring and is displayed in the main part of the image window 30. Depending upon the intention that is pursued, either the line camera 14 or the matrix camera 20 may be used for web monitoring. The use of the line camera 14 has the advantage that the position of the image area may be varied rapidly because no camera parts need to be moved mechanically and the part of the image to be captured only needs to be selected electronically. Although the line camera 14 has a digital zoom which permits to reproduce the selected image area on an increased scale, the resolution is limited because no optical zoom is available.

When certain parts of the image shall be monitored with highest resolution, it is recommended to use the matrix camera 20 the optical zoom of which permits to zoom-in very closely.

In the example shown in FIG. 2, the line camera 14 is used for monitoring. However, the matrix camera 20 is in stand-by, and the image area that would be photographed with the matrix camera 20 under the actual conditions (with low zoom factor) is indicated by a frame 40 in the small image 32.

When, for example, the print format includes two particularly critical areas to which particular attention should be paid in monitoring, it is possible to set the excerpt area monitored by the line camera 14 (frame 38) to one of these areas and the excerpt area monitored by the matrix camera 20 (frame 40) to the other area, so that web monitoring can be carried out with rapid switching between the two areas, without necessity to move any mechanical components. Likewise is it possible to reproduce several image areas simultaneously.

When, during web monitoring with the line camera 14, the operator discovers a local irregularity in the image that is reproduced in the main part of the image window 30 and wishes to inspect this irregularity with higher resolution, he may readily target the matrix camera 20 onto that spot and inspect the irregularity with high resolution. The position to which the matrix camera shall be driven may easily be input with a finger tip onto the place of interest on the screen.

On the other hand, it is also possible to use the matrix camera 20 for special tasks, e.g. an automatic quality monitoring of fixed motives in the printed image for which a particularly high print quality is required, e.g. company logos or bar codes on packaging material.

When, as in the example shown in FIG. 2, web monitoring is carried out with the line camera 14, the data stream provided by this line camera is automatically divided into two branch streams. One of these branch streams relates to the image area that has been selected for web monitoring and is reproduced in the image window 30 whereas the other branch stream includes the image information for the entire width of the web 10 and is stored together with the corresponding position information.

During the print run, the data processing system 16 performs, in parallel with the image reproduction for the web monitoring and in the background, an automatic error recognition algorithm on the basis of the data delivered by the line camera 14. When, in a certain area of the image printed onto the web 10, a deviation of the actually captured image from the reference image that has been sampled in a teach-in phase at the start of the print run is found and the deviation is beyond certain tolerance limits, the operating personal is alerted of this error already during the print run, e.g. by means of an acoustical signal and display of the defective image area on the screen 24. For increased attention, an enlarged image of the defective area may be blended-in into the image window 30 with a suitable animation effect.

In the example shown in FIG. 2, the operator has selected a mode of operation in which errors that have been detected automatically are only identified by suitable marks 42 in the small image 32. When the operator wants to interrupt the current web monitoring in order to have a closer look at the error indicated by the mark 42, he only needs to tip with his finger onto the corresponding mark on the touch screen 24, and he will obtain an enlarged image of the defective area in the window 30. When a particularly high zoom factor is required, this detail image may also be generated by the matrix camera 20 which will automatically move into the required position.

Figure 3:
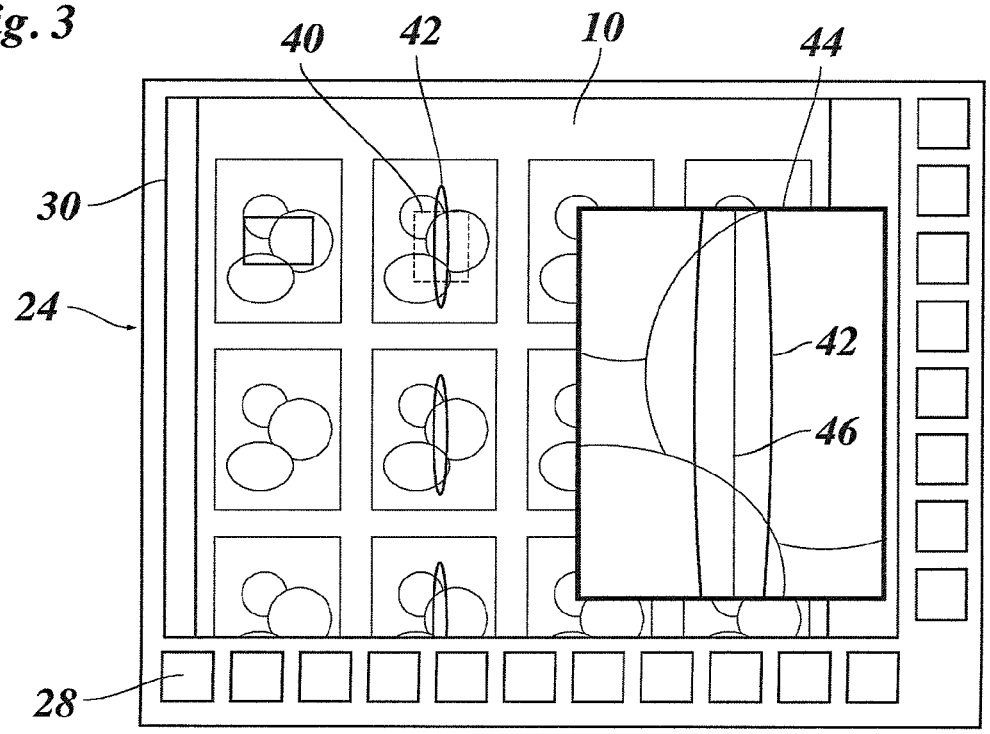

FIG. 3 illustrates a situation in which the user has selected a reproduction mode in which the section of the web 10 which had been shown in the small image 32 in FIG. 2 is now shown as a full-screen image in the window 30, and in which the area identified by the mark 42 is additionally displayed on a largely increased scale as "image in image" 44. In the example shown, the matrix camera 20 is used for that purpose, as is shown by the frame 40 in the main image. On the increased scale, the operator can recognize that the error that has automatically been detected is a doctor streak 46 in this example. He may now attempt to rectify this error by suitable remedies, e.g. a transverse movement or vibration of the doctor blade, and he may monitor the result on the screen 24.

If the doctor streak 46 cannot be removed, the operator may decide to abort the print run in order to clean the doctor blade.

This example illustrates the particular advantage of the integration of web monitoring and inspection in a common control desk in combination with automatic error recognition in the inspection system. Errors which would not have been noted in normal web monitoring can be recognized by the inspection system and can be indicated so timely that counter measures can be taken before large amounts of waste have been produced. The flexible image reproduction options make it easier for the user to identify and classify the error more closely, so that the counter measures may be targeted accordingly.

Preferably, the data processing system will also protocol the errors that have been detected in the automatic error detection and will store them as error images, so that, when the print run has been terminated, the errors may be inspected in detail at the control desk 18. Optionally, the control desk 18 may also control a winder with which the defective sections which have to be excised from the web 10 are brought into a suitable position on a cutting table.

What is claimed is:

1. An apparatus for monitoring a print result in a rotary printing press, comprising:
   a web monitoring system including a matrix camera that is movable in transverse direction over a printed web printed in the printing press, the matrix camera being adapted to capture an excerpt of the printed image in synchronism with a repeat of the printed image during a print run,
   an inspection system for a complete inspection of the printed image, said inspection system including a line camera that extends over the entire width of the web and adapted to capture a complete image of the printed web and storing the same in digital form which is linked with positional information indicating a location of a respective image area in a longitudinal direction of the web,
   an integrated control desk for the web monitoring system and the inspection system, and
   a data processing system adapted to automatically detect errors in the image printed onto the web by analyzing the image captured with the line camera and to display the errors visually on a screen of the control desk, the data processing system being adapted to indicate defective image areas by showing a mark on the screen and to interpret a strike of a user onto this mark as a command to display the image area where the error has been detected on an enlarged scale using the matrix camera.

2. The apparatus according to claim 1, wherein the control desk has a touch screen for selectively displaying at least one of:
   an image delivered by the matrix camera and
   an image delivered by the line camera
   and for inputting operating instructions.

3. The apparatus according to claim 1, wherein the matrix camera has an optical zoom function.

4. An apparatus for monitoring a print result in a rotary printing press, comprising:
   a web monitoring system including a matrix camera that is movable in transverse direction over a printed web printed in the printing press, the matrix camera being adapted to capture an excerpt of the printed image in synchronism with a repeat of the printed image during a print run,
   an inspection system for a complete inspection of the printed image, said inspection system including a line camera that extends over the entire width of the web and adapted to capture a complete image of the printed web and storing the same in digital form which is linked with positional information indicating a location of a respective image area in a longitudinal direction of the web, an integrated control desk for the web monitoring system and the inspection system, and a data processing system adapted to automatically detect errors in the image printed onto the web by analyzing the image captured with the line camera and to display the errors visually on a screen of the control desk, the data processing system being adapted to automatically adjust the matrix camera onto a position for a closer inspection of an error when such error has been detected in an automatic error detection process.

5. The apparatus according to claim 4, wherein the control desk has a touch screen for selectively displaying at least one of:

an image delivered by the matrix camera and an image delivered by the line camera and for inputting operating instructions.

6. The apparatus according to claim 4, wherein the matrix camera has an optical zoom function.

\* \* \* \* \*